US010441140B2

(12) United States Patent
Umemoto (10) Patent No.: US 10,441,140 B2
(45) Date of Patent: Oct. 15, 2019

(54) DRIVE SYSTEM, ENDOSCOPIC SYSTEM COMPRISING DRIVE SYSTEM, AND CONTROL DEVICE FOR DRIVE SYSTEM (71) Applicant: OLYMPUS CORPORATION, Tokyo (JP)

(72) Inventor: Yoshitaka Umemoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 99 days.

(21) Appl. No.: 15/391,322

(22) Filed: Dec. 27, 2016

(65) Prior Publication Data
US 2017/0105606 A1 Apr. 20, 2017

Related U.S. Application Data (63) Continuation of application No. PCT/JP2015/067490, filed on Jun. 17, 2015.

(30) Foreign Application Priority Data

Jun. 27, 2014 (JP) .................................. 2014-132771

(51) Int. Cl.
A61B 1/00 (2006.01)
G02B 23/24 (2006.01)
(Continued)

(52) U.S. Cl.
CPC .......... A61B 1/00133 (2013.01); A61B 1/005 (2013.01); A61B 1/00006 (2013.01);
(Continued)

(58) Field of Classification Search
CPC . G02B 23/24; A61B 1/00006; A61B 1/00009; A61B 1/00027; A61B 1/00112; A61B 1/005; A61B 1/04
(Continued)

(56) References Cited

U.S. PATENT DOCUMENTS 6,540,670 B1* 4/2003 Hirata ................. A61B 1/0051
600/146
2001/0025183 A1* 9/2001 Shahidi ................. A61B 90/10
606/130
(Continued)

FOREIGN PATENT DOCUMENTS

JP S62-181694 A 8/1987
JP H02-97290 A 4/1990
(Continued)

OTHER PUBLICATIONS

Extended Supplementary European Search Report dated Feb. 1, 2018 in European Patent Application No. 15 81 2428.9.
(Continued)

Primary Examiner — Timothy J Neal
Assistant Examiner — William B Chou
(74) Attorney, Agent, or Firm — Scully Scott Murphy & Presser, P.C.

(57) ABSTRACT

A control section outputs a control signal. An actuator is connected to a drive section and operates based on the control signal. An operation information acquisition section acquires operation information related to an operation status of the actuator. A storage section stores correction information included in control information which includes a relationship between an operation status and the control signal. The correction section determines whether or not the control signal and the operation status are consistent with the control information, and when inconsistent, corrects correction information for consistency.

10 Claims, 5 Drawing Sheets (51) Int. Cl.
  *A61B 1/005* (2006.01)
  *A61B 1/04* (2006.01)
(52) U.S. Cl.
  CPC ........ *A61B 1/00009* (2013.01); *A61B 1/0016* (2013.01); *A61B 1/00027* (2013.01); *A61B 1/00112* (2013.01); *A61B 1/04* (2013.01); *G02B 23/24* (2013.01)
(58) Field of Classification Search
  USPC ........ 600/102, 104, 109, 113, 114, 117, 118, 600/120, 160
  See application file for complete search history.

(56) References Cited

U.S. PATENT DOCUMENTS

| | | | | |
|---|---|---|---|---|
| 2002/0062062 A1* | 5/2002 | Belson | ................. | A61B 1/0053 600/146 |
| 2003/0097138 A1* | 5/2003 | Reydel | ............. | A61M 25/0043 606/108 |
| 2006/0176384 A1* | 8/2006 | Suda | ................. | H04N 5/23241 348/311 |
| 2008/0062261 A1* | 3/2008 | Sudo | ................. | A61B 1/00188 348/74 |
| 2010/0191056 A1* | 7/2010 | Tanaka | .................. | A61B 1/005 600/117 |
| 2010/0245549 A1* | 9/2010 | Allen | ................. | A61B 1/00183 348/65 |
| 2011/0166514 A1* | 7/2011 | Trovato | ............. | A61B 1/00133 604/95.01 |
| 2011/0234887 A1* | 9/2011 | Shimohata | ............... | G03B 3/10 348/353 |
| 2012/0071752 A1* | 3/2012 | Sewell | ..................... | A61B 6/12 600/424 |
| 2013/0161487 A1* | 6/2013 | Sakaguchi | ........ | H01L 27/14601 250/208.1 |
| 2014/0005667 A1* | 1/2014 | Stulen | .............. | A61B 17/32009 606/45 |
| 2014/0188081 A1* | 7/2014 | Saito | ...................... | A61B 1/005 604/525 |
| 2017/0049298 A1* | 2/2017 | Hunter | ................... | A61B 1/005 |

FOREIGN PATENT DOCUMENTS

| | | |
|---|---|---|
| JP | H06-33776 U | 5/1994 |
| JP | H07-140411 A | 6/1995 |
| JP | H09-166908 A | 6/1997 |
| JP | 2007-319547 A | 12/2007 |
| JP | 2011-221519 A | 11/2011 |

OTHER PUBLICATIONS

International Search Report dated Sep. 8, 2015 issued in PCT/JP2015/067490.

English translation of International Preliminary Report on Patentability dated Dec. 27, 2016 together with the Written Opinion received in related International Application No. PCT/JP2015/067490.

* cited by examiner

DRIVE SYSTEM, ENDOSCOPIC SYSTEM COMPRISING DRIVE SYSTEM, AND CONTROL DEVICE FOR DRIVE SYSTEM

CROSS-REFERENCE TO RELATED APPLICATIONS

This application is a Continuation Application of PCT Application No. PCT/JP2015/067490, filed Jun. 17, 2015 and based upon and claiming the benefit of priority from prior Japanese Patent Application No. 2014-132771, filed Jun. 27, 2014, the entire contents of all of which are incorporated herein by reference.

BACKGROUND OF THE INVENTION

1. Field of the Invention

The present invention relates to a drive system, an endoscopic system comprising the drive system, and a control device for the drive system.

2. Description of the Related Art

An endoscopic system, in which a rotary cylinder with a rotatable spiral convex portion is circumferentially provided on an insertion section, is disclosed, for example, in Jpn. Pat. Appln. KOKAI Publication No. 2007-319547. In Jpn. Pat. Appln. KOKAI Publication No. 2007-319547, the following technique is disclosed. In this endoscope, the rotary cylinder rotates around a longitudinal axis for the spiral convex portion to gather nearby tissues, and for the insertion section to advance or retreat in the longitudinal axis direction. Provided at the distal end portion and proximal end portion of such rotary cylinder are sensors for detecting the number of rotations. Based on the difference in the number of rotations between the distal end portion and the proximal end portion, the power supply to a motor for rotating the rotary cylinder is controlled.

In an endoscopic system which comprises a power unit such as the rotary cylinder mentioned above, in order to allow the insertion section to advance and retreat, it is necessary for a rotating body of the power unit to be able to rotate in both the forward and reverse directions. Here, preferably, the drive circuit including a power source and a configuration for switching directions of rotation should be simple. However, the rotation needs to be controlled with precision.

BRIEF SUMMARY OF THE INVENTION

According to one aspect of the present invention, the drive system comprises: a control section which outputs a control signal; a drive section which comprises a first terminal which outputs a first potential and a second terminal which outputs a second potential, in which the first potential and the second potential are based on the control signal, and the first potential and the second potential are both potentials which are higher than a reference potential or lower than the reference potential; an actuator which is connected between the first terminal and the second terminal, and is operable in a positive direction and a negative direction in accordance with a potential difference between the first potential and the second potential; an operation information acquisition section which acquires operation information related to an operation status of the actuator; a storage section which stores correction information included in control information which includes a relationship between the operation status and the control signal for obtaining such operation status; and a correction section which determines whether or not the control signal output from the control section and the operation status obtained based on the operation information are consistent with the control information, in which, when determined as inconsistent, a correction is performed on the correction information for consistency.

According to one aspect of the present invention, the endoscopic system comprises the drive system, an endoscope including an insertion section, and a power unit which is provided on the insertion section for advancing or retreating the insertion section and is driven by the actuator of the drive system.

According to one aspect of the present invention, a control device for a drive system comprises: a control section which outputs a control signal; a drive section which comprises a first terminal which outputs a first potential and a second terminal which outputs a second potential, in which the first potential and the second potential are based on the control signal, and the first potential and the second potential are both potentials which are higher than a reference potential or lower than the reference potential; an operation information acquisition section which acquires operation information related to an operation status of an actuator which is connected between the first terminal and the second terminal and is operable in a positive direction and a negative direction in accordance with a potential difference between the first potential and the second potential; a storage section which stores correction information included in control information which includes a relationship between the operation status and the control signal for obtaining such operation status; and a correction section which determines whether or not the control signal output from the control section and the operation status obtained based on the operation information are consistent with the control information, in which, when determined as inconsistent, a correction is performed on the correction information for consistency.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
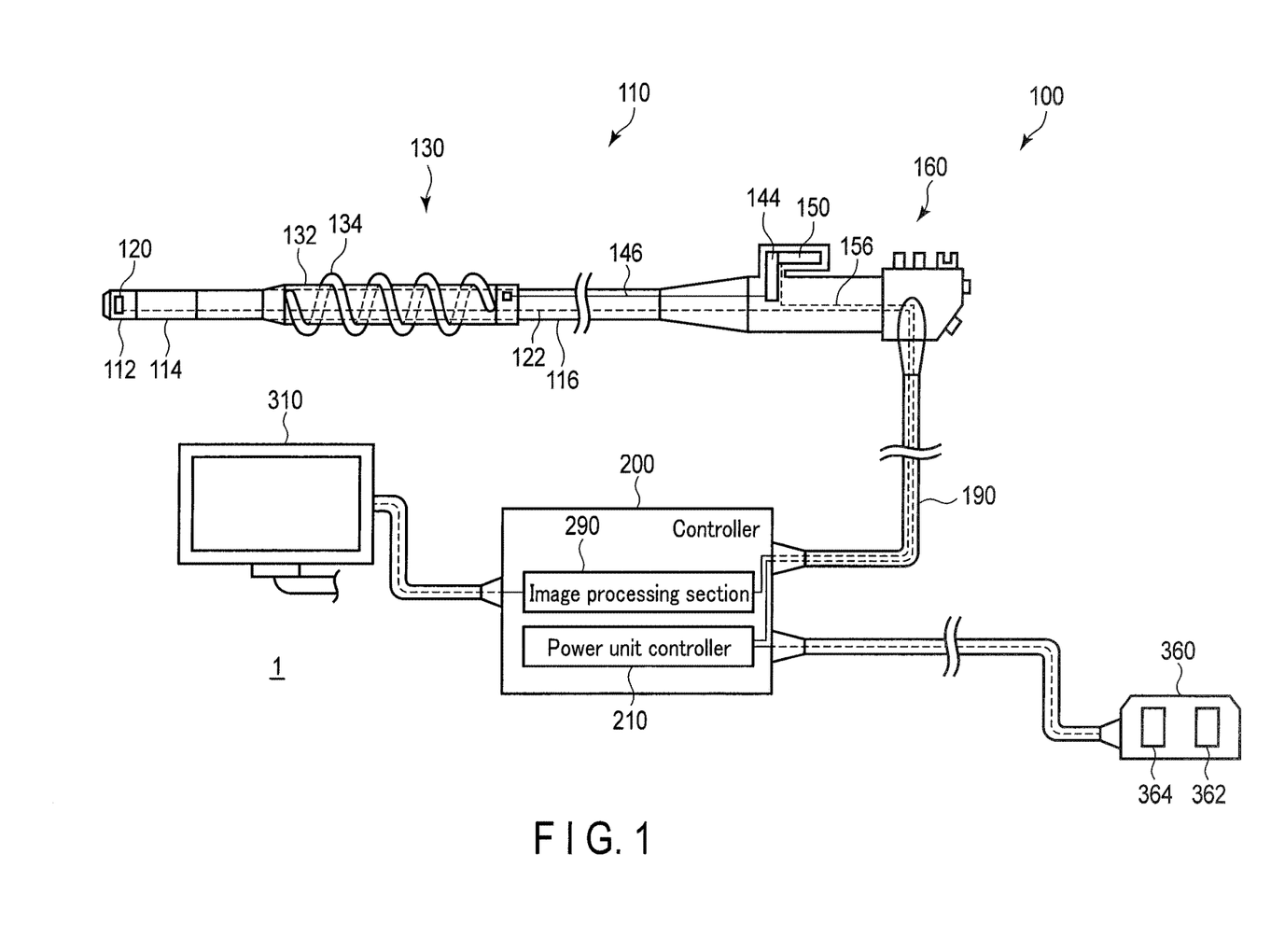
FIG. 1 is a schematic view of a configuration example of a living body introduction apparatus according to an embodiment of the present invention.

The first embodiment of the present invention will be explained with reference to the drawings. A schematic view of a configuration of a living body introduction apparatus 1 is shown in FIG. 1 as an endoscopic system according to the present embodiment. As shown in this drawing, the living body introduction apparatus 1 comprises an endoscope 100, a controller 200, a monitor 310, and an input section 360. The endoscope 100 comprises an elongated shape insertion section 110 configured to be inserted into a living body. The endoscope 100 also comprises an operation section 160 for performing various kinds of operations of the endoscope 100. The operation section 160 is held by a user. Here, a distal end side of the insertion section 110 will be referred to as a distal end side, and the operation section 160 side will be referred to as a proximal end side. The operation section 160 of the endoscope 100 and the controller 200 are connected by a universal cable 190.

The insertion section 110 comprises a distal rigid section 112 provided at the most distal end, a bending section 114 provided at the proximal end side of the distal rigid section 112, and an insertion tube 116 provided at the proximal end side of the bending section 114. The bending section 114 is configured to actively bend in accordance with the rotation of an unillustrated operation knob provided on the operation section 160. The insertion tube 116 bends passively by external force.

On the distal rigid section 112 is provided an imaging element 120. The imaging element 120 generates an image signal based on, for example, a subject image at the distal end side of the insertion section 110. The image signal acquired at the imaging element 120 is transmitted to the controller 200 via a signal line for imaging signals 122 which is passed through the insertion section 110 and the universal cable 190. The distal rigid section 112 is also provided with an unillustrated illumination window for illuminating a subject. The illumination window is connected to an unillustrated light guide which extends from the controller. A light emitted from a light source provided inside the controller is guided by the light guide and is emitted from the illumination window. The subject is illuminated by the light emitted from the illumination window. The distal rigid section 112 is also provided with an opening section of a treatment tool channel tube through which a treatment tool, such as forceps, is passed.

A power unit (a spiral unit) 130 is attached to the insertion tube 116 of the insertion section 110. The power unit 130 comprises a cylindrical attachment unit (base tube) 132 provided rotatably around a longitudinal axis of the insertion tube 116 on the circumference of the insertion tube 116. On the outer periphery of the attachment unit 132 is provided a fin 134. The fin 134 is provided spirally about the longitudinal axis of the attachment unit 132. The fin 134 rotates in accordance with the rotation of the attachment unit 132.

The attachment unit 132 is connected to the actuator 150 provided on the operation section 160 via a gear inside a gear box 144 and a drive shaft 146. When the actuator 150 is operated by an operation using the input section 360, its drive force is transmitted by the gear inside the gear box 144 and the drive shaft 146. As a result, the attachment unit 132 and the fin 134 can be rotated clockwise and counter-clockwise around the longitudinal axis thereof.

When the attachment unit 132 and the fin 134 rotate in a state where the fin 134 is in contact with a wall portion, such as, for example, a wall of a lumen, a propulsive force acts on the insertion section 110 towards a distal end side or a proximal end side. For example, in the small intestine and the large intestine, the propulsive force acts on the insertion section 110 by the fin pulling on the folds present on the inner wall of the small intestine and the large intestine. Such propulsive force improves insertability and decannulation of the insertion section 110 at the lumen.

The monitor 310 is a general display element such as, for example, a liquid crystal display. The monitor 310 displays, for example, an endoscopic image under the control of the image processing unit 290 explained later on.

The input section 360 includes, for example, a foot switch. The input section 360 includes a first input section 362 and a second input section 364 configured by an analogue switch, etc. The living body introduction apparatus 1 is configured in a manner that, when the first input section 362 is turned on, the actuator 150 is operated to rotate the fin 134, for example, clockwise. The living body introduction apparatus 1 is also configured in a manner that, when the second input section 364 is turned on, the actuator 150 is operated to rotate the fin 134, for example, counter-clockwise. As a result, when the first input section 362 is turned on, the insertion section 110 advances to the distal end side, and when the second input section 364 is turned on, the insertion section 100 retreats to the proximal end side. In this manner, a user's instruction is input to the input section 360. The signal output from the input section 360 will be referred to as an adjustment signal. The input section 360 outputs an adjustment signal with a value corresponding to the degree of depression on the foot switch by the user. Based on this value, the rotation speed of the fin 134 is controlled.

The controller 200 performs control of each section of the living body introduction apparatus 1. The controller 200 comprises an image processing section 290. The image processing section 290 acquires an image signal from the imaging element 120 and applies necessary image processing to the image. The image processing section 290 outputs the image processed image signal to the monitor 310 and has the monitor 310 display the image.

The controller 200 comprises a power unit controller 210 which functions as a control device for controlling the operation of the power unit 130. The actuator 150 and the power unit controller 210 are connected by a signal line for actuator current signals 156.

Figure 2:
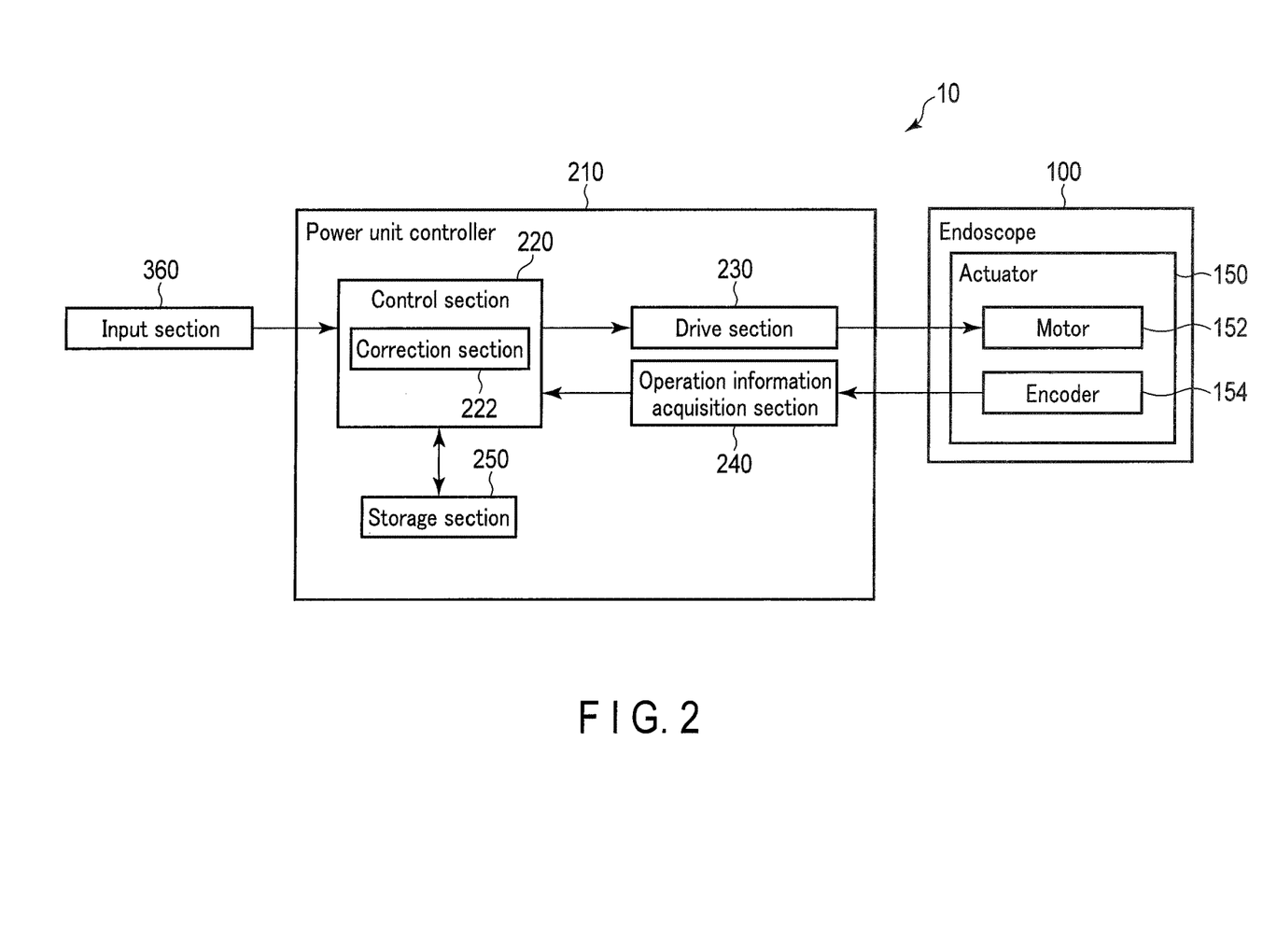
FIG. 2 is a block diagram schematically showing a configuration example of a power unit control section.

A configuration focusing on the power unit controller 210 will be explained with reference to the block diagram shown in FIG. 2. The actuator 150 provided in the endoscope 100 comprises a motor 152 which functions as an actuating device and an encoder 154. The motor 152 is a power source for operating the power unit 130. The attachment unit 132 of the power unit 130 rotates clockwise and counter-clockwise in order to advance and retreat the insertion section 110. Therefore, the motor 152 rotates clockwise and counter-clockwise. In the present embodiment, the motor 152 is a direct-current motor. The encoder 154 detects the amount of rotation of the motor 152.

The power unit controller 210 comprises a control section 220, a drive section 230, an operation information acquisition section 240, and a storage section 250.

The control section 220 includes, for example, a CPU or an ASIC. The control section 220 acquires from the input section 360 an adjustment signal presenting information related to a rotation direction and a rotation speed of the motor 152 the user desires. The control section 220 adjusts the control signal output to the drive section 230 based on the adjustment signal acquired from the input section 360. The control section 220 outputs this control signal to the drive section 230.

For the control according to the present embodiment, a control signal utilizing a pulse width modulation (PWM) is used. In other words, a square wave is output from the control section 220 to the drive section 230. The output of the control section 220 is a one-line output using one terminal. That is, the number of connection wires between the control section 220 and the drive section 230 is one. The square wave output from the control section 220 is a signal of, for example, 0V and 5V.

The control section 220 also includes a correction section 222 for correcting the control signal to drive the motor 152 correctly in the manner explained later on. The correction section 222 determines correction information included in the control information that is necessary for driving the motor 152 correctly. Here, the control information is information including the relationship between the control signal output from the control section 220 and a driving amount of the motor 152. The correction information is information for correcting the relationship included in this control information. The control section 220 creates the control signal using the control information including the determined correction information.

The storage section 250 stores the control information including the relationship between the control signal output from the control section 220 and the driving amount of the motor 152, and the correction information which is information for correcting the control information included in this control information. The correction information is changed as needed by the correction section 222.

The drive section 230 includes a circuit which drives the motor 152 based on the square wave input from the control section 220. An example of a circuit configuration of the drive section 230 will be explained with reference to FIG. 3.

Figure 3:
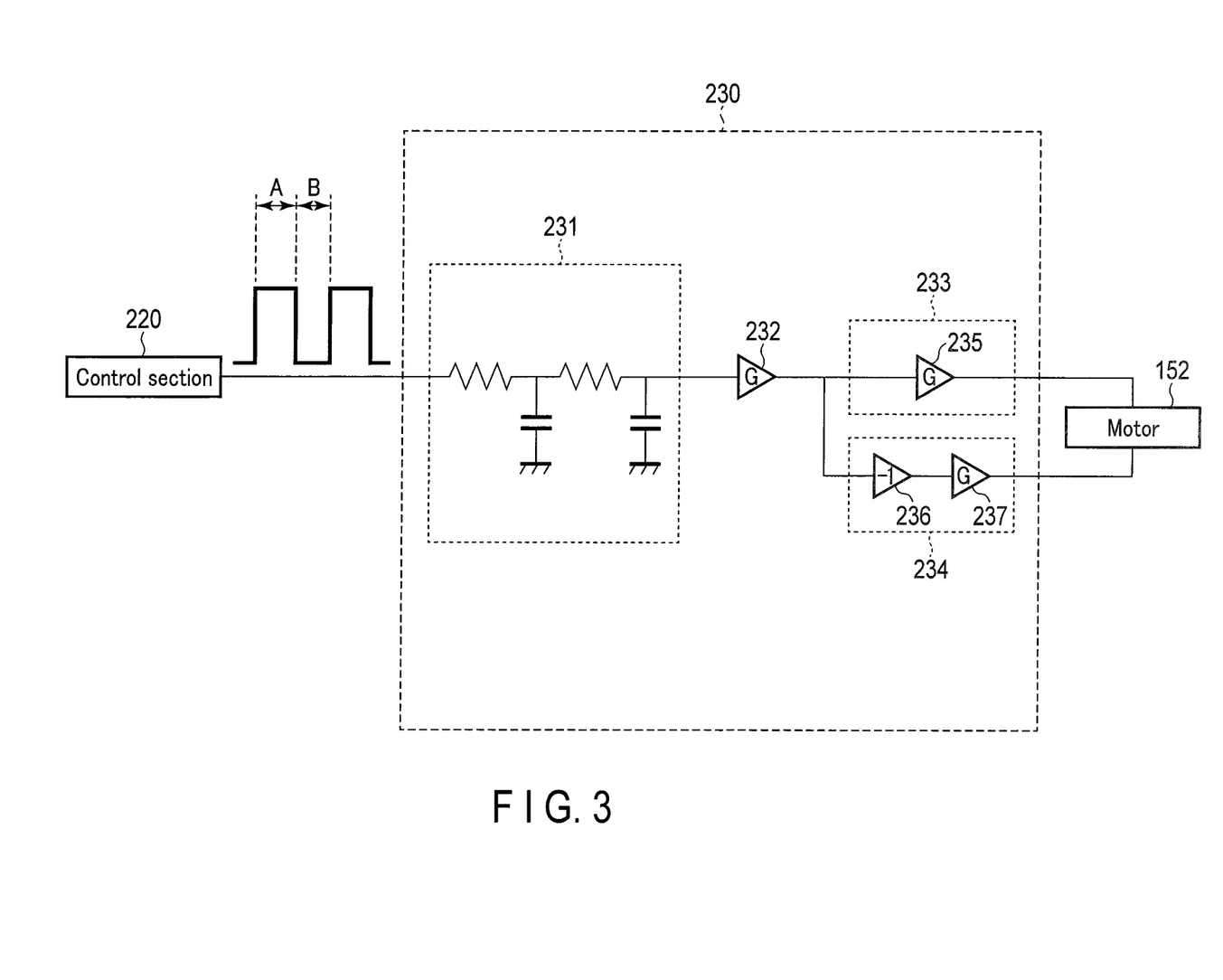
FIG. 3 is a schematic view of a configuration example of a drive section according to a first embodiment.

An output terminal of the control section 220 is connected to an input terminal of the drive section 230. To the input terminal of the drive section 230 is connected a low-pass filter 231. The low-pass filter 231 is provided with two stages of low-pass filters comprising a resistor and a condenser. In other words, the low-pass filter 231 has a configuration in which two sets of low-pass filters having a configuration in which the resistor is connected between the input end and the output end, and the condenser is connected between the output end and a ground, are connected in series. The square wave output from the control section 220 is first FV-converted by the low-pass filter 231. In other words, as shown in FIG. 3, when a ratio between a pulse width A in an ON-state and a pulse width B in an OFF-state of the square wave output from the control section 220 is regarded as a duty ratio, the square wave would be converted by the low-pass filter 231 into a voltage value corresponding to the duty ratio. For example, when the duty ratio is 100:0, the output terminal of the low-pass filter 231 would be 5V, when the duty ratio is 50:50, the output terminal of the low-pass filter 231 would be 2.5V, and when the duty ratio is 0:100, the output terminal of the low-pass filter 231 would be 0V.

To the output terminal of the low-pass filter 231 is connected an input terminal of a first amplifier 232. The signal that has passed the low-pass filter 231 is amplified in accordance with a gain of the first amplifier 232.

To an output terminal of the first amplifier 232 is connected in parallel a first circuit 233 and a second circuit 234. The first circuit 233 includes a second amplifier 235. The first circuit 233 increases a potential of the signal amplified at the first amplifier 232 by a predetermined value. The second circuit 234 includes a circuit configuration in which an inverting amplifier 236 with a gain of −1 and a third amplifier 237 are connected in series. The second circuit 234 has the potential of the signal amplified at the first amplifier 232 inverted, and increases the potential by a predetermined value. The output terminal of the first circuit 233 and the output terminal of the second circuit 234 are respectively connected to the input terminals of the motor 152.

The circuit of the drive section 230 is adjusted in a manner so that an output value commensurate with the duty ratio of the control signal output from the control section 220 becomes a ratio between the output terminal of the first circuit 233 and the output terminal of the second circuit 234. For example, when a rated voltage of the motor 152 is 24V, the following adjustment is carried out. When the duty ratio of the control signal is 90:10, the output terminal of the first circuit 233 becomes 27V, and the output terminal of the second circuit 234 becomes 3V. At this time, a voltage of +24V is applied to the motor 152. When the duty ratio of the control signal is 50:50, the output terminal of the first circuit 233 becomes 15V, and the output terminal of the second circuit 234 becomes 15V. At this time, no voltage is applied to the motor 152. When the duty ratio of the control signal is 10:90, the output terminal of the first circuit 233 becomes 3V, and the output terminal of the second circuit 234 becomes 27V. At this time, a voltage of −24V is applied to the motor 152. In this manner, the drive section 230 functions as a drive section comprising a first terminal which outputs a first potential that is higher than a ground potential based on a control signal, and a second terminal which outputs a second potential that is higher than the ground potential based on the control signal.

The drive section 230 applies to the motor 152 a voltage corresponding to the duty ratio of the square wave output from the control section 220. According to a configuration as that of the drive section 230, a power source may only be a power source on the plus side, and the output terminal of the control section 220 may be set to one. In other words, by comprising a one-wire type configuration, the number of used output terminals of the control section 220 configured using, for example, CPU may be reduced to only one pin. In the above manner, the circuit according to the present embodiment comprises an extremely simple configuration. Furthermore, high response and linearity of an analog circuit exercise advantages in the present embodiment which performs speed control of the power unit 130. Although the power source has been described as being only on the plus side, the power source may be only on the minus side.

Hypothetically, in the case where one of the terminals of the motor 152 is connected to ground, in order to rotate the motor 152 forwards and backwards, it is necessary to input a plus voltage value and a minus voltage value to the other terminal of the motor 152. In this case, a plus power source and a minus power source would be required. In contrast, according to the present embodiment, a minus power source would be unnecessary.

Furthermore, there is also a method of, when rotating the motor 152 forwards, connecting one of the terminals to the plus side and the other terminal to ground, and, when rotating the motor 152 backwards, connecting the one of the terminals to ground and the other terminal to the plus side. However, hypothetically, in a case where such configuration is adopted, for example, a switching circuit using a field-effect transistor would be required. In contrast, according to the present embodiment, a switching circuit would be unnecessary. As a result, signals for controlling the switching circuit would become unnecessary, and the number of output terminals of the control section 220 may be reduced.

Here, an example of a circuit which rotates the motor 152 forwards and backwards by only a plus power source or a minus power source has been explained; however, the circuit configuration of the drive section 230 is not limited to this. In a case where a plus power source and a minus power source can be prepared, the degree of freedom of the circuit configuration of the drive section 230 would increase. Even in a case where the plus power source and the minus power source can be prepared, the drive section 230 may function as a drive section comprising a first terminal which outputs a first potential that is higher than a reference potential based on the control signal, and a second terminal which outputs a second potential that is higher than the reference potential based on the control signal. In this case, the drive section 230 may also function as a drive section comprising a first terminal which outputs a first potential that is lower than a reference potential based on the control signal, and a second terminal which outputs a second potential that is lower than the reference potential based on the control signal. In other words, the drive section 230 may be configured in a manner so that an output value corresponding to a duty ratio of a control signal output from the control section 220 is output from the first terminal and the second terminal. Furthermore, in a case where the plus power source and the minus power source can be prepared, the drive section 230 may take the form of various circuit configurations, which is a simple one-wire type in which the control section 220 has one output terminal.

The explanation will continue by returning to FIG. 2. The operation information acquisition section 240 acquires the output of the encoder 154 and, based on the output of this encoder, acquires operation information related to the operation status of the motor. The operation information acquisition section 240 outputs the acquired operation information to the control section 220. The operation information related to the operation status of the motor 152 is used for a feedback control performed by the control section 220. In other words, the control section 220 controls the operation of the motor 152 by speed control using information of the rotation amount of the motor 152 acquired by the operation information acquisition section 240.

The operation information acquired by the operation information acquisition section 240 is also used for correcting the control signal which is a square wave. For example, ideally, when the duty ratio is 50:50, both voltages of the output terminals of the first circuit 233 and the second circuit 234 become 15V, and the motor 152 would stop. However, depending on individual differences of each element included in the drive section 230, aging of its property, and environment such as temperature, etc., in some cases, the motor 152 may rotate even if a square wave with a duty ratio of 50:50 is input to the drive section 230 from the control section 220. Therefore, in the power unit controller 210 of the present embodiment, the output of the control section 220 is corrected to prevent the motor 152 from performing unintended operations. In other words, based on the output value of the operation information acquisition section 240, in a case where the motor 152 is detected as slightly rotating forward when the duty ratio is 50:50, for example, the correction section 222 of the control section 220 performs correction so that the duty ratio for immobilizing the motor 152 becomes 49:51. The correction information mentioned above is, for example, information indicating that it is necessary to correct the duty ratio for immobilizing the motor 152 from 50:50 to 49:51. By carrying out the above correction, the operation of the motor 152 may be controlled correctly.

If an element with a high degree of accuracy is used for the element included in the drive section 230, there is a possibility that the above-mentioned correction would become unnecessary. However, in such case, the cost of the entire device would increase. In contrast, according to the present embodiment, a device performing appropriate operations may be manufactured inexpensively. Such correction would be essential upon shipment of the device. Such correction is also preferred to be performed automatically on start-up of the device.

In the above manner, the drive system 10 for advancing and retreating the insertion section 110 of the endoscope 100 includes the power unit controller 210, the actuator 150, and the input section 360.

The operation of the living body introduction apparatus 1 according to the present embodiment will be explained. The living body introduction apparatus 1 is used for observing, for example, inside a body cavity. When using the living body introduction apparatus 1, a user, for example, grips the operation section 160 with the left hand and inserts the insertion section 110 into the body of a subject to be examined while holding the insertion tube 116 with the right hand. Furthermore, the user operates the input section 360 which is, for example, a foot switch by foot to rotate the fin 134, and to advance or retreat the insertion section 110. Here, the user operates the living body introduction apparatus 1 while observing the monitor 310.

Figure 4:
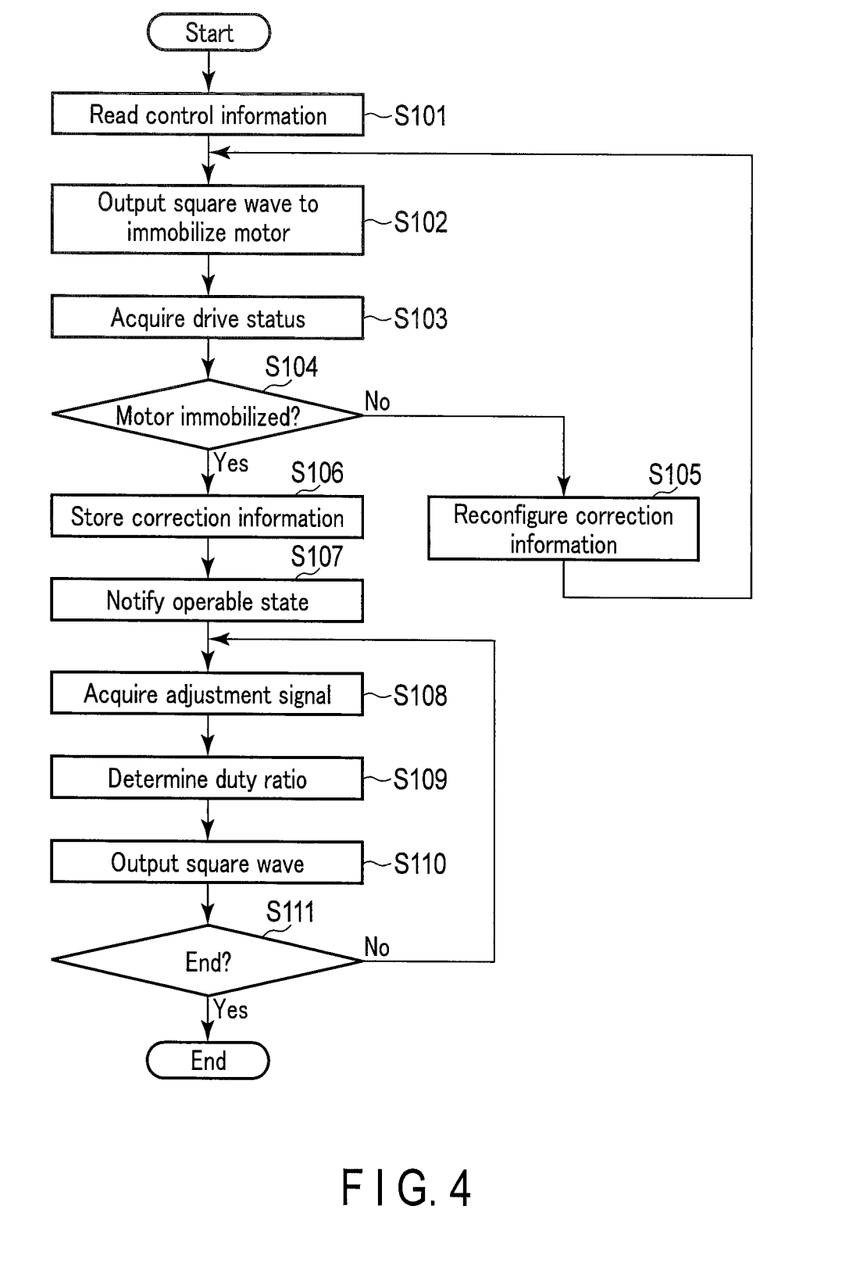
FIG. 4 is a flowchart showing an operation example of the power unit control section according to the first embodiment.

An operation of the power unit controller 210 will be explained with reference to the flowchart shown in FIG. 4. This control is implemented when, for example, the controller 200 is powered on. First of all, the above-mentioned correction is carried out.

In step S101, the control section 220 acquires control information including the latest correction information stored in the storage section 250.

In step S102, the control section 220 outputs a square wave for immobilizing the motor 152 as a control signal based on the acquired control information. For example, when correction is unnecessary, the control section 220 outputs a square wave with a duty ratio of 50:50. In step S103, based on the output of the encoder 154, the control section 220 acquires operation information related to the operation status of the current motor 152 which has been calculated by the operation information acquisition section 240.

In step S104, the control section 220 determines whether or not the motor 152 is immobilized. When the motor 152 is determined as not immobilized, the process proceeds to step S105. In step S105, the control section 220 reconfigures the correction information. Subsequently, the process returns to step S102. Therefore, subsequently, the output of the control signal is performed based on the control information which includes the reconfigured correction information. For example, as a square wave for immobilizing the motor 152, a square wave with a duty ratio of 49:51 would be output.

When the motor 152 is determined as being immobilized in the determination of step S104, the process proceeds to step S106. In step S106, the control section 220 stores the currently used correction information in the storage section 250. In step S107, the control section 220 notifies that it is operable. For example, the control section 220 has the monitor 310 display the operable status. Hereafter, the power unit 130 is operated in accordance with the operation by a user. At this time, the control information in which the correction information is updated is used.

In step S108, the control section 220 acquires an adjustment signal based on the input to the input section 360. Information related to whether the fin 134 should be rotated forwards or backwards, and the rotation amount thereof is input to the input section 360 by the user. The adjustment signal is a signal presenting this information. In step S109, the control section 220 determines the duty ratio of the control signal based on the adjustment signal and the control information. In step S110, the control section 220 outputs the square wave of the determined duty ratio as the control signal. As a result, the motor 152 is rotated and the power unit 130 operates.

In step S111, the control section 220 determines whether or not an ending instruction has been input. The ending instruction is input, for example, when the use of the power unit 130 has ended. When it is determined that the ending instruction is not input, the process returns to step S108. On the other hand, when the ending instruction is determined as being input, the process is ended.

According to the present embodiment, the motor 152 may be controlled correctly even if the number of connection wires between the control section 220 and the drive section 230 is set to one, and, further, the drive section 230 has an inexpensive circuit configuration. Since the correction mentioned above is carried out only by adjusting the duty ratio of the control signal which is a square wave output from the control section 220, the circuit configuration of the drive section 230 does not need to be complicated. Furthermore, according to the correction carried out by adjusting the duty ratio, in comparison to a case in which correction is carried out by using a voltage value which is a digital value, etc., a highly accurate correction may be easily realized. Furthermore, although an output of the encoder 154 is used for the correction, since the encoder 154 is originally necessary for controlling the operation of the motor 152, this would not be considered as newly adding a constituent element to the drive system 10 for correction.

In the example mentioned above, the correction is performed under the condition that the motor 152 is immobilized. However, it is not limited to this case. The correction may be made based on the control signal and the operation information when rotating the motor 152 at a predetermined speed.

In the embodiment mentioned above, an example of performing speed control by controlling the drive of the motor 152 based on the output of the encoder 154 is explained. However, the control method is not limited to this. In consideration of the load to a living body, a torque control using a current value flowing in the motor 152 and a voltage value applied to the motor 152, etc. may also be used. In other words, in speed control, when the rotation of the fin 134 is disturbed by a surrounding living tissue, there is a possibility that a high load may be applied to the living tissue. In contrast, in torque control, the load applied to the living tissue is limited. In this case, since an output value of the encoder 154 is not required for the control, it may not always be monitored. The configuration of the drive system 10 of the present embodiment exercises advantages even in the case where the output value of the encoder 154 is not always monitored in the manner above.

In the embodiment mentioned above, the operation status of the motor 152 is acquired based on the output of the encoder 154. However, it is not limited to this case. For example, the potential of the output terminal of the first circuit 233 and the potential of the output terminal of the second circuit 234 may be acquired to use these values as operation information indicating the operation status of the motor 152. In other words, correction may be carried out so that the relationship between the potential difference of the output terminal of the first circuit 233 and the output terminal of the second circuit 234, and that of the control signal becomes a predetermined relationship.

The drive system 10 of the present embodiment has been explained as a system for driving the power unit 130. However, it is not limited to this case; and, therefore, the technique according to the present embodiment may be used for a drive system that drives various units. For example, the technique according to the present embodiment may also be used for driving a bending structure of an electric bending endoscope. In accordance with its usage, the motor 152 as an actuator may be replaced by other power sources.

Second Embodiment

The second embodiment will be explained. Here, the difference from the first embodiment will be explained. For identical portions, identical symbols will be applied, and the explanations thereof will be omitted. In the control according to the first embodiment, a control signal utilizing a pulse-width modulation is used, and a square wave is output from the control section 220 to the drive section 230. In contrast, in the present embodiment, an analog signal is output from the control section 220.

Figure 5:
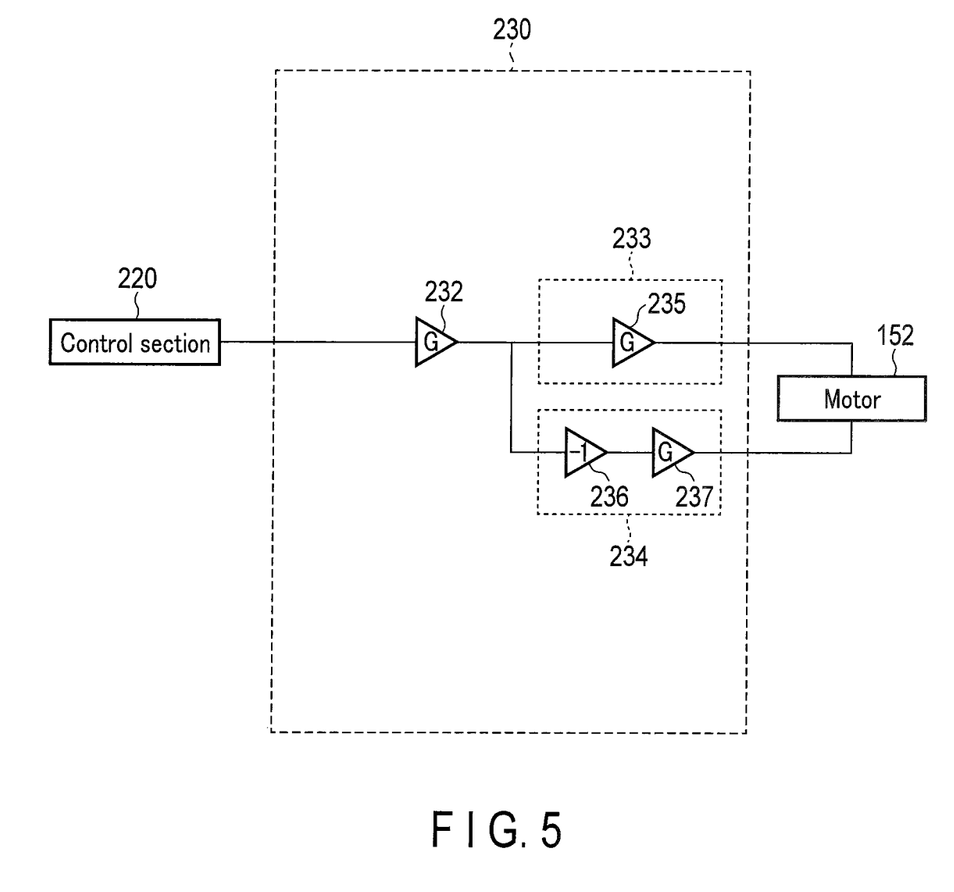
FIG. 5 is a schematic view of a configuration example of a drive section according to a second embodiment.

An example of a circuit configuration of a drive section 230 according to the present embodiment is shown in FIG. 5. As shown in FIG. 5, in comparison to the drive section 230 of the first embodiment, there is no low-pass filter 231 for converting the pulse-width signal into an analog signal. The other circuit configurations are the same as those in the drive section 230 of the first embodiment. In other words, the analog signal output from the control section 220 is input to a first amplifier 232.

In the present embodiment, the following points are different from the first embodiment in the process explained with reference to FIG. 4. In step S102, the control section 220 outputs an analog signal having a voltage value for immobilizing the motor 152 as the control signal. For example, a case in which the control section 220 is capable of outputting a voltage value from 0V to 5V will be considered. When correction is not required, the control section 220 outputs a voltage of 2.5V. In step S104, when the motor 152 is determined as not immobilized, correction information is reconfigured in step S105. In other words, the output of the control section 220 in step S102 is changed to, for example, 2.4V.

Furthermore, in step S109, the control section 220 determines the output voltage value based on the adjustment signal and the control signal. In step S110, the control section 220 outputs the analog signal having the determined output voltage value as the control signal. As a result, the motor 152 is rotated and the power unit 130 operates.

The present embodiment is also capable of controlling the motor 152 correctly even if the number of connection wires between the control section 220 and the drive section 230 is set to one, and the drive section 230 also has a simple and inexpensive circuit configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic system comprising:
   an endoscope comprising an insertion section;
   at least one control circuit configured to output a control signal, wherein the control signal is a one-line output using one terminal of the at least one control circuit;
   a drive circuit comprising:
      a first terminal configured to output a first potential which is higher than a ground potential based on the control signal; and
      a second terminal configured to output a second potential which is higher than the ground potential based on the control signal;
   an actuator connected between the first terminal and the second terminal, wherein the actuator is configured to be operable in a positive direction and a negative direction in accordance with a potential difference between the first potential and the second potential;
   a spiral provided on the insertion section, wherein the spiral is configured to be driven by the actuator in order to advance and retreat the insertion section; and
   a memory,
   wherein the at least one control circuit is configured to store operation information related to an operation status of the actuator,
   wherein the memory is a configured to store correction information included in control information which includes a relationship between the operation status and the control signal for obtaining the operation status, and
   wherein the at least one control circuit is configured to:
      determine whether or not the control signal and the operation status obtained based on the operation information are consistent with the control information; and
      in response to determining that the control signal and the operation status obtained based on the operation information are inconsistent, perform correction with respect to the correction information for consistency.

2. The endoscopic system according to claim 1, further comprising:
   one connection wire between the at least one control circuit and the drive circuit,
   wherein the drive circuit comprises an inverting circuit and is configured to output the first potential and the second potential based on the control signal input through the one connection wire from the at least one control circuit.

3. The endoscopic system according to claim 2,
   wherein the actuator comprises a direct current motor configured to be rotatable forward and backward.

4. The endoscopic system according to claim 3, further comprising an encoder configured to acquire a driving amount of the actuator,
   wherein the at least one control circuit is configured to acquire the driving amount as the operation information.

5. The endoscopic system according to claim 2,
   wherein the at least one control circuit is configured to perform the correction based on the operation status of when the at least one control circuit is outputting the control signal for immobilizing the actuator.

6. The endoscopic system according to claim 1,
   wherein the control signal utilizes a pulse-width modulation, and
   wherein the drive circuit is configured to:
      output from the first terminal the first potential which is based on a duty ratio of the control signal; and
      output from the second terminal the second potential based on the duty ratio of the control signal.

7. The endoscopic system according to claim 6,
   wherein the at least one control circuit is configured to determine a duty ratio of the control signal for immobilizing the actuator.

8. The endoscopic system according to claim 1,
   wherein the at least one control circuit is configured to acquire the first potential and the second potential as the operation information.

9. The endoscopic system according to claim 1, further comprising an input device configured to output an adjustment signal for changing the control signal in accordance with an input,
   wherein the at least one control circuit is configured to perform the correction before the adjustment signal is input.

10. A control device for an endoscopic system, the control device comprising:
    at least one control circuit configured to output a control signal, wherein the control signal is a one-line output using one terminal of the at least one control circuit;
    a drive circuit comprising:
       a first terminal configured to output a first potential which is higher than a ground potential based on the control signal; and
       a second terminal configured to output a second potential which is higher than the ground potential based on the control signal; and
    a memory,
    wherein the at least one control circuit is connected between the first terminal and the second terminal, and is configured to store operation information related to an operation status of an actuator which is operable in a positive direction and a negative direction in accordance with a potential difference between the first potential and the second potential,
    wherein the memory is configured to store correction information included in control information which includes a relationship between the operation status and the control signal for obtaining the operation status, and
    wherein the at least one control circuit is configured to:
       determine whether or not the control signal and the operation status obtained based on the operation information are consistent with the control information; and
       in response to determining that the control signal and the operation status obtained based on the operation information are inconsistent, perform correction with respect to the correction information for consistency.

* * * * *